United States Patent
Colvin, Jr.

(10) Patent No.: US 9,377,351 B2
(45) Date of Patent: Jun. 28, 2016

(54) ANGLE OF INCIDENCE SELECTIVE BAND PASS FILTER FOR IMPLANTABLE CHEMICAL SENSOR

(71) Applicant: Senseonics, Incorporated, Germantown, MD (US)

(72) Inventor: Arthur E. Colvin, Jr., Mt. Airy, MD (US)

(73) Assignee: Senseonics, Incorporated, Germantown, MD (US)

( * ) Notice: Subject to any disclaimer, the term of this patent is extended or adjusted under 35 U.S.C. 154(b) by 389 days.

(21) Appl. No.: 13/869,279

(22) Filed: Apr. 24, 2013

(65) Prior Publication Data

US 2013/0324819 A1 Dec. 5, 2013

Related U.S. Application Data

(60) Provisional application No. 61/637,549, filed on Apr. 24, 2012.

(51) Int. Cl.

| | |
|---|---|
| *A61B 5/1455* | (2006.01) |
| *G01J 1/06* | (2006.01) |
| *G01N 21/64* | (2006.01) |
| *A61B 5/145* | (2006.01) |
| *A61B 5/1459* | (2006.01) |
| *G01J 1/42* | (2006.01) |
| *G02B 6/04* | (2006.01) |
| *G01J 1/04* | (2006.01) |
| *G01J 3/02* | (2006.01) |
| *G01J 1/16* | (2006.01) |

(Continued)

(52) U.S. Cl.
CPC ................ *G01J 1/06* (2013.01); *A61B 5/1451* (2013.01); *A61B 5/1459* (2013.01); *A61B 5/14532* (2013.01); *A61B 5/14551* (2013.01); *G01J 1/0214* (2013.01); *G01J 1/0425* (2013.01); *G01J 1/1626* (2013.01); *G01J 1/42* (2013.01); *G01J 3/0218* (2013.01); *G01J 3/0262* (2013.01); *G01N 21/64* (2013.01); *G01N 21/645* (2013.01); *G01N 21/6428* (2013.01); *G02B 6/04* (2013.01); *G01J 1/0488* (2013.01); *G01J 2001/062* (2013.01); *G01N 2021/6432* (2013.01); *G02B 6/08* (2013.01)

(58) Field of Classification Search
CPC ............. A61B 5/1455; A61B 5/14551; A61B 5/14532; A61B 5/1459
See application file for complete search history.

(56) References Cited

U.S. PATENT DOCUMENTS

| | | | |
|---|---|---|---|
| 4,244,045 A * | 1/1981 | Nosu et al. ...................... | 398/86 |
| 4,755,667 A | 7/1988 | Marsoner et al. | |

(Continued)

FOREIGN PATENT DOCUMENTS

WO 2010/033901 A1 3/2010

*Primary Examiner* — Eric Winakur (74) *Attorney, Agent, or Firm* — Rothwell, Figg, Ernst & Manbeck, P.C.

(57) ABSTRACT

Apparatuses and methods for limiting the angle of incidence (AOI) of light reaching a dichroic filter. The apparatus may include an AOI filter element and the dichroic filter. The apparatus may be a sensor and may include a photodetector. The dichroic filter may be configured to prevent light having a wavelength outside a band pass region from reaching the photodetector and to pass light having a wavelength within the band pass. Physical limitations of the dichroic filter may preclude the dichroic filter from preventing high AOI light having a wavelength outside a band pass region from reaching the photodetector. The AOI filter element may be configured to prevent light having a high AOI from reaching the dichroic band pass filter and to propagate light having a low AOI to the dichroic band pass filter. The AOI filter element may be a fiber optic bundle comprising a plurality of optical fibers.

33 Claims, 8 Drawing Sheets

(51) Int. Cl.
*G01J 1/02* (2006.01)
*G02B 6/08* (2006.01)

(56) References Cited

U.S. PATENT DOCUMENTS

| | | |
|---|---|---|
| 5,543,870 A | 8/1996 | Blanchard |
| 5,893,364 A * | 4/1999 | Haar et al. .................. 600/310 |
| 5,917,605 A | 6/1999 | Colvin, Jr. |
| 6,285,807 B1 | 9/2001 | Walt et al. |
| 6,330,464 B1 | 12/2001 | Colvin, Jr. et al. |
| 6,791,687 B1 | 9/2004 | Rushbrooke et al. |
| 8,351,041 B2 * | 1/2013 | Leveque et al. ............... 600/476 |
| 2004/0071332 A1 | 4/2004 | Bruce et al. |
| 2005/0035304 A1 | 2/2005 | Colvin, Jr. et al. |
| 2005/0207943 A1 | 9/2005 | Puzey |
| 2006/0231749 A1 | 10/2006 | Colvin et al. |
| 2008/0186494 A1 | 8/2008 | Kiesel et al. |

* cited by examiner

ANGLE OF INCIDENCE SELECTIVE BAND PASS FILTER FOR IMPLANTABLE CHEMICAL SENSOR

CROSS-REFERENCE TO RELATED TO APPLICATION

The present application claims the benefit of priority to U.S. Provisional Application Ser. No. 61/637,549, filed on Apr. 24, 2012, which is incorporated herein by reference in its entirety.

BACKGROUND

1. Field of Invention

The present invention relates to angle of incidence filtering. In particular, the present invention relates to limiting the angle of incidence of light incident towards a dichroic band pass filter in connection with an implantable optical sensor.

2. Discussion of the Background

A sensor may be implanted within a living animal (e.g., a human) to measure the concentration of an analyte (e.g., glucose or oxygen) in a medium (e.g., interstitial fluid (ISF) or blood) within the living animal. Examples of implantable sensors employing indicator molecules to measure the concentration of an analyte are described in U.S. Pat. No. 6,330,464, which is incorporated herein by reference in its entirety.

Figure 1:
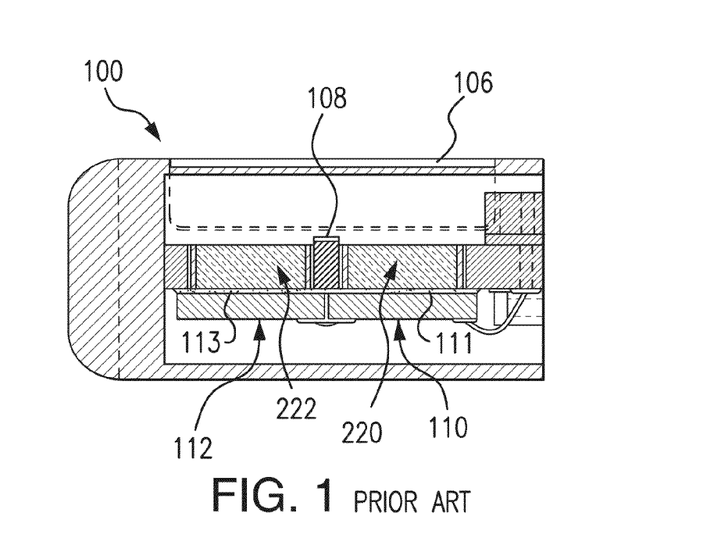
FIG. 1 is a cross-sectional view of an example of an existing sensor.
Figure 2:
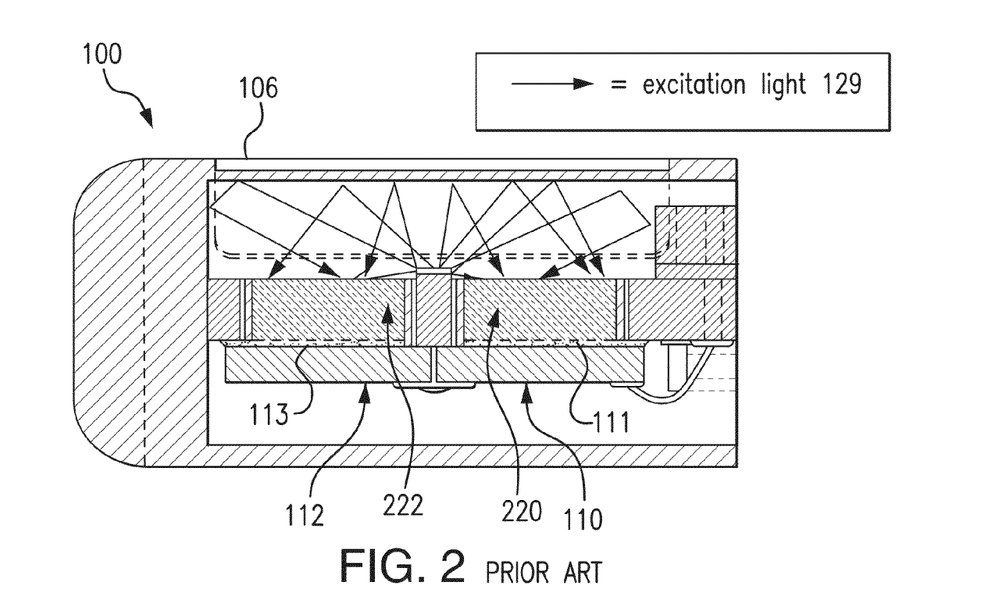
FIG. 2 is a cross-sectional view of the example of an existing sensor in operation.

FIG. 1 illustrates a cross-sectional view of an example of an existing sensor 100. FIG. 2 illustrates a cross-sectional view of the existing sensor 100 in operation. The sensor 100 includes a light source 108 that emits excitation light 129 to a graft 106 containing indicator molecules. The indicator molecules have an optical characteristic that varies based on the concentration of the analyte in the medium. In particular, when excited by the excitation light 129, indicator molecules that have bound the analyte emit (i.e., fluoresce) light having a wavelength different than the wavelength of the excitation light 129. The sensor 100 includes a first dichroic band pass filter 111 (thin film) that filters light incident on a first photodetector 110. The first dichroic band pass filter 111 is designed to only pass light having the wavelength of the light emitted by the indicator molecules so that, in theory, the first photodectector 110, which is a signal photodetector, only receives the light emitted by the indicator molecules.

In sensors having multiple channels (e.g., a signal channel and a reference channel) and/or multiple photodiodes, the sensor may include a dichroic band pass filter for each channel and/or photodetector. For instance, as shown in FIGS. 1 and 2, existing sensor 100 includes a second dichroic band pass filter 113 (thin film) that filters light incident on a second photodetector 112. The second dichroic band pass filter 113 is designed to only pass light having the wavelength of reference light so that, in theory, the second photodetector 112, which is a reference photodetector, only receives the reference light.

In the existing sensor 100, the dichroic band pass filters 111 and 113 are coated directly onto the surface of each photodetector (e.g., photodiode). In existing sensor 100, light (e.g., reflected excitation light 129 and fluorescent light emitted by the indicator molecules in the graft 106) passes through one or more glass windows 220 and 222. Each of the glass windows 220 and 222 may be a clad rod, which may be glued onto a dichroic band pass filter coated photodetector using optical epoxy.

As noted above, excitation light 129 from the light source 108 serves to excite the fluorescent indicator molecules within the surface graft 106. When excitation light 129 is absorbed by the indicator molecules, its energy is converted to analyte modulated fluorescence, which may be detected by the signal channel (e.g., including first photodetector 110). For excitation light 129 that is not absorbed (e.g., because it did not encounter an indicator molecule), that light may either be reflected within the system, or it may be backscattered and ultimately enter the glass windows (clad rods) 220 and 222 and be propagated through the windows 220 and 222 and onto the dichroic filters 111 and 113 coated onto the surface of each photodetector 110 and 112, and ultimately passed into the photodiode where the energy from that backscattered or reflected photon is also converted to current that is then indistinguishable from the analyte modulated signal. Inside the existing sensor 100, because of backscatter, natural edge emission from the light source 108, simple reflections from materials within the device 100, and the principle of total internal reflection within the encasement, excitation light 129 can propagate through the waveguide at all angles. FIG. 2 illustrates the variety of angles at which the reflected excitation light 129 may enter the glass windows (clad rods) 220 and 222 before being propagated onto the dichroic filters 111 and 113.

The performance of the sensor 100 may be degraded when light other than the analyte modulated light, which is emitted by excited indicator molecules in the graft 106, enters the first/signal channel photodetector 110 and is measured thereby. Similarly, in sensors 100 having a reference channel, the performance of the device may be degraded when light other than the reference light enters the second/reference channel photodetector 112 and is measured thereby. That is, unwanted light is noise which may compromise the performance, accuracy, and/or sensitivity of the sensor 100.

Because of the physical limitation of incident light angle sensitivity of dichroic film type filters, unwanted backscatter or reflected excitation light 129 at high angles of incidence in the signal channel may be a significant source of noise, drift, and elevated baseline in the existing sensor 100. Accordingly, there is a need for sensors having improved accuracy and in which these problems are substantially reduced or eliminated.

SUMMARY

The present invention overcomes the disadvantages of prior systems by providing, among other advantages, an angle of incidence filter element to prevent light having high angles of incidence from reaching a dichroic filter and, therefore, prevent the light having high angles of incidence from reaching the photodetector. That is, the angle of incidence filter element may act as a precollimator/prefilter on the light before it reaches the dichroic filter so that only light within acceptable angles of incidence reaches the dichroic film filter, and the dichroic filter can operate within its physical limitations to achieve its specified/intended bandpass filtering to allow only bandpass filtered light to reach the photodetector.

One aspect of the present invention provides a sensor comprising a photodetector, a dichroic band pass filter, and an angle of incidence filter element. The photodetector may be configured to convert received light into current indicative of the intensity of the received light. The dichroic band pass filter may be configured to prevent light having a wavelength outside a band pass region from reaching the photodetector and to pass light having a wavelength within the band pass region to the photodetector. The angle of incidence filter element may comprise a receiving surface and may be configured to prevent light having an angle of incidence relative to an axis perpendicular to the receiving surface greater than a threshold angle from reaching the dichroic band pass filter and to propagate light having an angle of incidence relative to the axis perpendicular to the receiving surface less than the threshold angle to the dichroic band pass filter. The angle of incidence filter element may be a fiber optic bundle comprising a plurality of optical fibers.

In some embodiments, each of the plurality of optical fibers may comprise a core having a first refractive index and a clad having a second refractive index that is lower than the first refractive index. A relative value of the first and second refractive indices may define the threshold angle. The fiber optical bundle may have been cut into a fiber optic plate.

In some embodiments, the sensor may further comprise indicator molecules and a light source. The indicator molecules may be configured to emit emission light at least to the receiving surface of the angle of incidence filter element. The light source configured to irradiate excitation light to the indicator molecules. The indicator molecules may be positioned relative to the receiving surface of the angle of incidence filter element such that at least a portion of the emission light reaches the receiving surface of the angle of incidence filter element with an angle of incidence relative to the axis perpendicular to the receiving surface less than the threshold angle.

In some embodiments, the dichroic band pass filter may be a thin film dichroic band pass filter. The dichroic band pass filter may be coated on the angle of incidence filter element. The angle of incidence filter element may comprise an exit surface opposite the receiving surface, and the dichroic band pass filter may be coated on the exit surface of the angle of incidence filter element. The dichroic band pass filter may be coated on the photodetector.

In some embodiments, the photodetector may be a photodiode. The threshold angle is less than or equal 30 degrees and greater than or equal to 5 degrees. The threshold angle may be less than or equal to 20 degrees and greater than or equal to 10 degrees. The threshold angle may less than or equal to 17 degrees and greater than or equal to 12 degrees. The threshold angle may be 15 degrees. The threshold angle may be 10 degrees. The threshold angle may be less than or equal to an angle of incidence relative to the axis perpendicular to the receiving surface of the angle of incidence filter element at which the spectral performance of the dichroic band pass filter begins to break down. The threshold angle may be configured to optimize the optical signal to noise ratio (SNR) of the light received by the photodetector, analyte modulated light may be the signal, and all other unwanted incident light may be the noise.

In some embodiments, the photodetector may be a first photodetector, the dichroic band pass filter may be a first dichroic band pass filter, the band pass region may be a first bandpass region, the receiving surface may be a first receiving surface, the threshold angle may be a first threshold angle, and the sensor may comprise a second photodetector, a second dichroic band pass filter, and a second angle of incidence filter element.

In some embodiments, the second photodetector may be configured to convert received light into current indicative of the intensity of the light received by the second photodetector. The second dichroic band pass filter may be configured to prevent light having a wavelength outside a second band pass region from reaching the second photodetector and to pass light having a wavelength within the second band pass region to the second photodetector. The second angle of incidence filter element may comprise a second receiving surface and may be configured to prevent light having an angle of incidence relative to an axis perpendicular to the second receiving surface greater than a second threshold angle from reaching the second dichroic band pass filter and to propagate light having an angle of incidence relative to the axis perpendicular to the second receiving surface less than the second threshold angle to the second dichroic band pass filter.

Another aspect of the present invention provides a method of detecting the concentration of an analyte using a sensor comprising a light source, indicator molecules, an angle of incidence filter element, a dichroic band pass filter, and a photodetector. The method may include irradiating, by the light source, excitation light to the indicator molecules; emitting, by the indicator molecules, emission light to the angle of incidence filter element. The method may include receiving, by a receiving surface of the angle of incidence filter element, light including the emission light; preventing, by the angle of incidence filter element, light of the received light having an angle of incidence greater than a threshold angle relative to an axis perpendicular to the receiving surface from reaching the dichroic band pass filter. The method may include propagating, by the angle of incidence filter element, light of the received light having an angle of incidence less than the threshold angle relative to the axis perpendicular to the receiving surface. The method may include preventing, by the dichroic band pass filter, light of the propagated light having a wavelength outside a band pass region of the dichroic band pass filter from reaching the photodetector. The method may include passing, by the dichroic band pass filter, light of the propagated light having a wavelength within the band pass region of the dichroic band pass filter to the photodetector. The method may include receiving, by the photodetector, the passed light.

In some embodiments, the angle of incidence filter element may be a fiber optic bundle comprising a plurality of optical fibers. Each of the plurality of optical fibers may comprise a core and a clad having refractive indices whose relative value defines the threshold angle. The fiber optical bundle may have been cut into a fiber optic plate.

In some embodiments, at least a portion of the emission light may reach the receiving surface of the angle of incidence filter element with an angle of incidence relative to the axis perpendicular to the receiving surface less than the threshold angle. The threshold angle may be less than or equal 20 degrees and greater than or equal to 5 degrees. The threshold angle may be less than or equal to 20 degrees and greater than or equal to 10 degrees. The threshold angle may be less than or equal to 17 degrees and greater than or equal to 12 degrees. The threshold angle may be 15 degrees. The threshold angle may be 10 degrees. The threshold angle may be 20 degrees. The threshold angle may be less than or equal to an angle of incidence relative to the axis perpendicular to the receiving surface of the angle of incidence filter element at which the spectral performance of the dichroic band pass filter begins to break down. The threshold angle may be configured to optimize the optical signal to noise ratio (SNR) of the light received by the photodetector, analyte modulated light may be the signal, and all other unwanted incident light may be the noise.

An additional aspect of the present invention provides an apparatus comprising a dichroic band pass filter and an angle of incidence filter element. The dichroic band pass filter may be configured to prevent light having a wavelength outside a band pass region from passing through the dichroic band pass filter and to pass light having a wavelength within the band pass region. The angle of incidence filter element may comprising a receiving surface and may be configured to prevent light having an angle of incidence relative to an axis perpendicular to the receiving surface greater than a threshold angle from reaching the dichroic band pass filter and to propagate light having an angle of incidence relative to the axis perpendicular to the receiving surface less than the threshold angle to the dichroic band pass filter. The angle of incidence filter element may be a fiber optic bundle comprising a plurality of optical fibers.

In some embodiments, the apparatus may be a sensor.

Still another aspect of the present invention may provide a method of filtering light using an apparatus comprising an angle of incidence filter element and a dichroic band pass filter. The method may include receiving, by a receiving surface of the angle of incidence filter element, light. The method may include preventing, by the angle of incidence filter element, light of the received light having an angle of incidence greater than a threshold angle relative to an axis perpendicular to the receiving surface from reaching the dichroic band pass filter. The method may include propagating, by the angle of incidence filter element, light of the received light having an angle of incidence less than the threshold angle relative to the axis perpendicular to the receiving surface. The method may include preventing, by the dichroic band pass filter, light of the propagated light having a wavelength outside a band pass region of the dichroic band pass filter from passing through the dichroic band pass filter. The method may include passing, by the dichroic band pass filter, light of the propagated light having a wavelength within the band pass region of the dichroic band pass filter. The angle of incidence filter element may be a fiber optic bundle comprising a plurality of optical fibers.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 3:
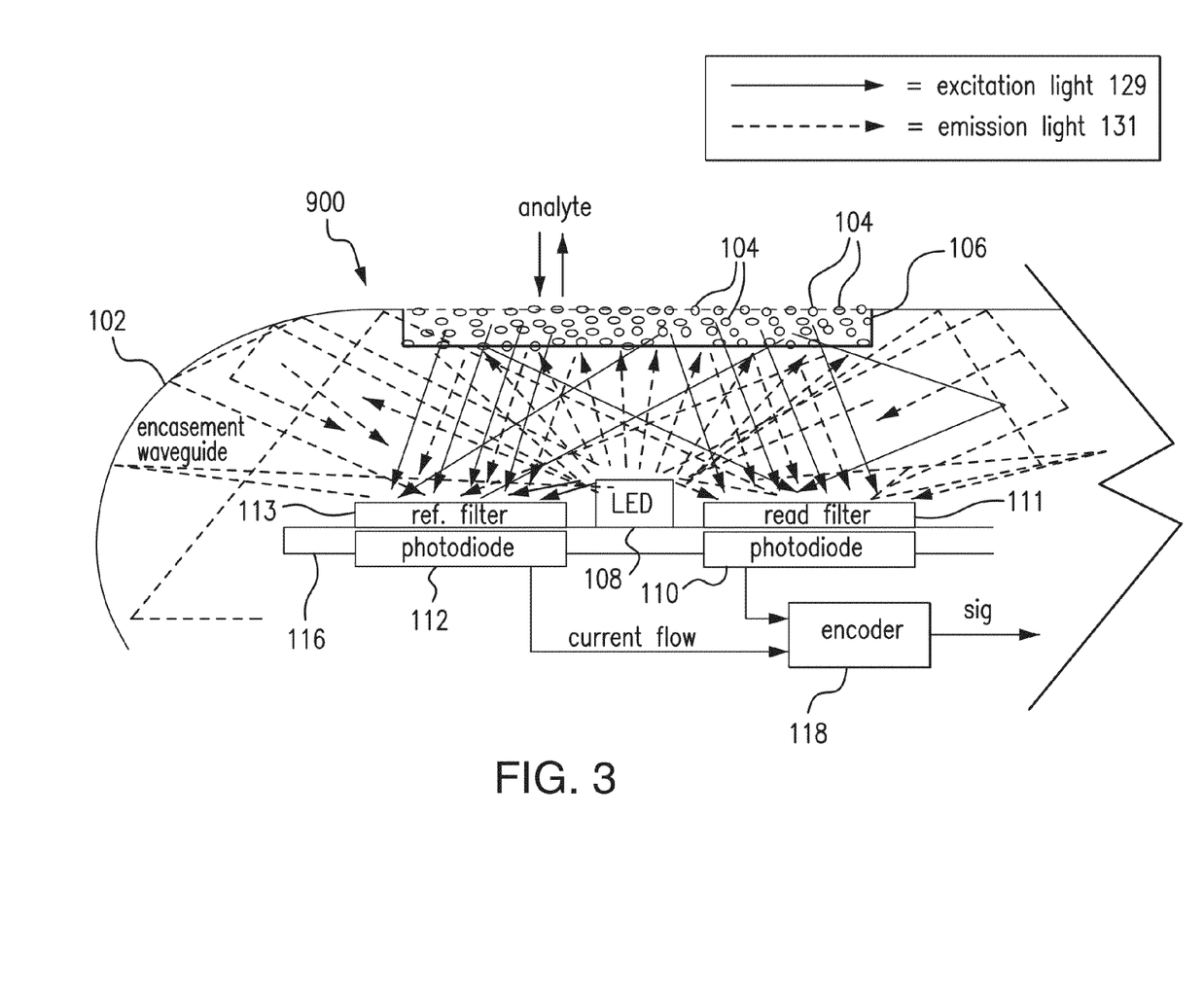
FIG. 3 is a schematic view of a sensor embodying aspects of the present invention.
Figure 4:
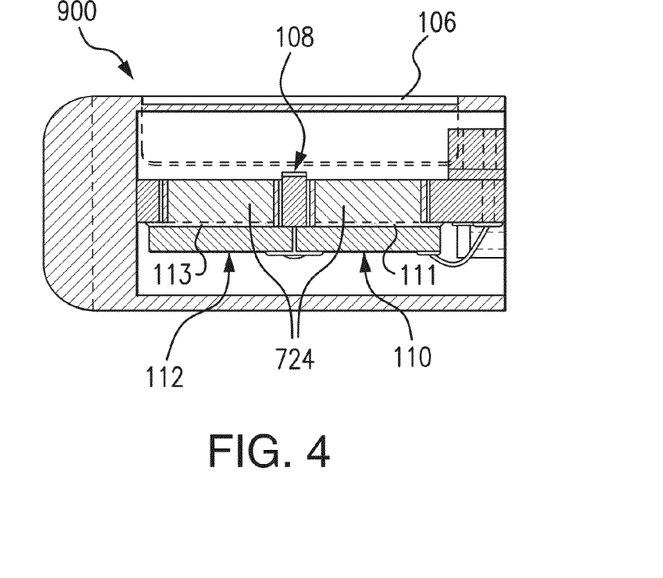
FIG. 4 is a cross-sectional view of a sensor embodying aspects of the present invention.

FIG. 3 is a schematic view of a sensor 900 embodying aspects of the present invention. FIG. 4 is a cross-sectional view of one non-limiting embodiment of the sensor 900. In some embodiments, the sensor 900 may be an implantable optical chemical sensor. In a non-limiting embodiment, the sensor 900 may be a highly miniaturized dual channel precision fixed wavelength fluorimeter. The sensor 900 may be implanted, for example, in a living animal's arm, wrist, leg, abdomen, or other region of the living animal suitable for sensor implantation. For example, the sensor 900 may be implanted between the skin and subcutaneous tissues.

In some embodiments, the sensor 900 may wirelessly receive power and data (e.g., commands) from an external sensor reader (not shown), and the sensor 900 may wirelessly convey analyte (e.g., glucose) readings to the external sensor reader. For example, the sensor 900 and external sensor reader may each include an inductive element (e.g., a coil). The inductive elements of the sensor 900 and external sensor reader may be in any configuration that permits adequate field strength to be achieved when the two inductive elements are brought within adequate physical proximity. The inductive element of the external sensor reader may generate an electromagnetic wave or electrodynamic field, which induce a current in the inductive element of the sensor 900. The induced current may power the sensor 900. The sensor reader may convey data by modulating the electromagnetic wave used to power the sensor 900 (e.g., by modulating the current flowing through the inductive element of the external sensor reader). The modulation in the electromagnetic wave generated by the external sensor reader may be detected/extracted by the sensor 900. Moreover, the sensor 900 may convey data (e.g., measurement information) to the external sensor reader by, for example, modulation an electromagnetic wave generated by the inductive element of the sensor 900. In some embodiments, an encoder 118 may encode the data before it is conveyed to the external sensor reader.

The sensor 900 may include a sensor housing 102 (i.e., body, shell, capsule, or encasement), which may be rigid and biocompatible. The sensor housing 102 may be formed from a suitable, optically transmissive polymer material, such as, for example, acrylic polymers (e.g., polymethylmethacrylate (PMMA)). The sensor housing 102 may be any shape suitable for implantation into a living animal. For instance, the sensor housing 102 may be cylindrical, pill-shaped, disc-shaped, spherical, or rectangular prism-shaped.

In some embodiments, the sensor 900 may include indicator molecules 104. The indicator molecules 104 may be fluorescent indicator molecules (e.g., Trimethyltrifluromethylsilane (TFM) fluorescent indicator molecules) or absorption indicator molecules. The indicator molecules 104 may reversibly bind an analyte (e.g., glucose). When an indicator molecule 104 has bound the analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no glucose is bound, the indicator molecule 104 may be only weakly fluorescent.

In some embodiments, the sensor 900 may include a polymer graft/matrix layer 106 coated, diffused, adhered, or embedded on at least a portion of the exterior surface of the sensor housing 102, with the indicator molecules 104 distributed throughout the polymer graft 106. The polymer graft 106 may be a fluorescent analyte indicating polymer. The polymer may be biocompatible and stable, grafted onto the surface of sensor housing 102, designed to allow for the direct measurement of interstitial fluid (ISF) glucose after subcutaneous implantation of the sensor 900.

In some embodiments, the sensor 900 may include a light source 108, which may be, for example, a light emitting diode (LED) or other light source, that emits radiation, including radiation over a range of wavelengths that interact with the indicator molecules 104. In other words, the light source 108 may emit the excitation light 129 that is absorbed by the indicator molecules 104 in the polymer graft 106. As noted above, the light source 108 may emit excitation light 329 that is ultraviolet (UV) light (e.g., light with a wavelength of approximately 378 nm). The graft 106 may be positioned to receive excitation light 129 emitted by the light source 108.

The sensor 900 may also include one or more photodetectors (e.g., photodiodes, phototransistors, photoresistors or other photosensitive elements). For example, as illustrated in FIGS. 3 and 4, the sensor 900 may have a first photodetector 110 and a second photodetector 112. The first and second photodetectors 110 and 112 may be arrayed symmetrically on either side of the light source 108. The first photodetector 110 may be a signal photodetector (i.e., read photodetector), and the second photodetector 112 may be a reference photodetector. However, the sensor 900 is not required to have more than one photodetector, and some alternative sensors 900 may only include the first photodetector 110.

Some part of the excitation light 129 emitted by the light source 108 may be reflected or backscattered from the polymer graft 106 back into the sensor 900, and some part of the absorbed excitation light may be emitted as emitted (fluoresced) light 131. The emitted light 131 may have a different wavelength (e.g., higher or lower) than the wavelength of the excitation light 129. The reflected excitation light 129 and emitted (fluoresced) light 131 may be absorbed by the one or more photodetectors (e.g., first and second photodetectors 110 and 112) within the body of the sensor 900.

In some embodiments, the sensor 900 may include one or more filters (e.g., a filters 111 and 113). As illustrated in FIGS. 3 and 4, each of the one or more photodetectors may be covered by a filter. Each of the one or more filters may allow only a certain subset of wavelengths of light to pass through. In some embodiments, the one or more filters may be thin glass filters. In some embodiments, the one or more filters may be thin film (dichroic) filters deposited on the glass and may pass only a narrow band of wavelengths and otherwise reflect most of the light.

As illustrated in FIGS. 3 and 4, the first photodetector 110 may be covered by a signal filter 111. The signal filter 111 may be configured to pass a narrow band of wavelengths including the wavelength of the emission light 131 emitted (e.g., fluoresced) by the indicator molecules 104 in the graft 106. For instance, the peak emission of the indicator molecules 104 may occur around 435 nm, and the signal filter 111 may pass light in the range of 400-500 nm and prevent other light from reaching the first photodetector 110 (e.g., by reflecting most of the light outside the 400-500 nm range). However, this is not required, and, in other sensors 900, the emission light 131 may have a different peak emission wavelength, and/or the signal filter 111 may pass light in a different (e.g., narrower, expanded, or shifted) wavelength range.

The second photodetector 112 may be covered by a reference filter 113. The reference filter 113 may be configured to pass a narrow band of wavelengths including the wavelength of a reference light. In one non-limiting embodiment, the reference light passed by the reference filter 113 may have the same wavelength as the excitation light 129 (e.g., 378 nm), and the reference filter 113 may pass light in a narrow band (e.g., 350-400 nm) including the wavelength of the excitation light 129 and prevent other light from reaching the second photodetector 112. However, this is not required, and, in other embodiments, the reference light passed by the reference filter 113 may have a different wavelength than the excitation light 129 (e.g., the wavelength of light emitted by reference indicator molecules that are unaffected or generally unaffected by the presence and/or concentration of the analyte), and/or the reference filter 113 may pass light in a different (e.g., narrower, expanded, or shifted) wavelength range.

In some embodiments, the first photodetector 110 may be configured to (a) receive the emission light 131 that is emitted from the indicator molecules 104 in the graft 106 and (b) generate a signal indicative of the amount of light received thereby. Higher analyte (e.g., glucose or oxygen) levels/concentrations may correspond to a greater amount of emission light 131 (e.g., fluorescence) of the indicator molecules 104 in the graft 106, and, therefore, a greater number of photons striking the first photodetector 110.

In some embodiments, the second photodetector 112 may be configured to receive the reference light and generate a signal indicative of the amount of light received thereby. In some embodiments, the reference light may have the same wavelength as the excitation light 129 emitted by the light source 108 and, as illustrated in FIG. 3, may include a portion of the excitation light 129 that is reflected from the graft 106. In some alternative embodiments, the reference light may have a different wavelength than the excitation light 129 (e.g., the wavelength of light emitted by reference indicator molecules that are unaffected or generally unaffected by the presence and/or concentration of the analyte).

In some embodiments, the substrate 116 may be a circuit board (e.g., a printed circuit board (PCB)) on which circuit components (e.g., analog and/or digital circuit components) may be mounted or otherwise attached. However, as an alternative, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components. Circuitry of the sensor 900 may incorporate some or all of the structure described in U.S. patent application Ser. No. 13/650,016, which is incorporated herein by reference in its entirety, with particular reference to FIG. 11D or U.S. patent application Ser. No. 13/761,839, which is incorporated herein by reference in its entirety, with particular reference to FIG. 6.

Figure 5:
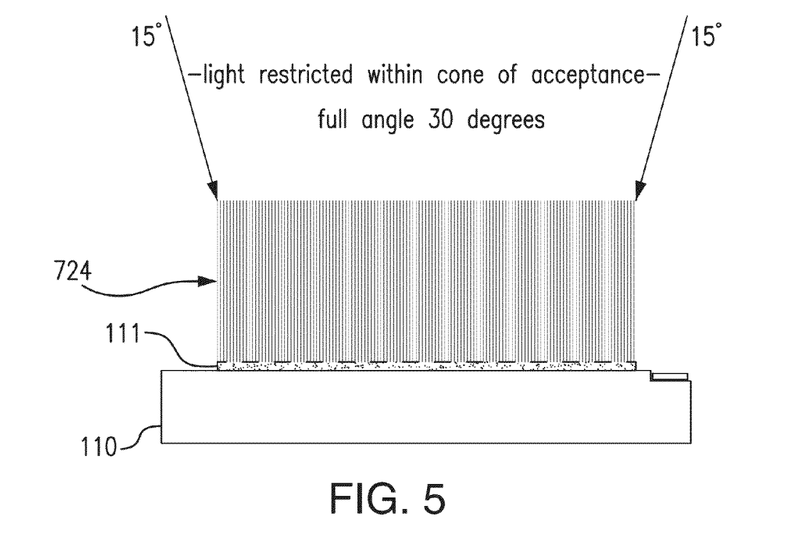
FIG. 5 is a cross-sectional view illustrating an AOI filter element, dichroic filter, and photodetector embodying aspects of the present invention.
Figure 6:
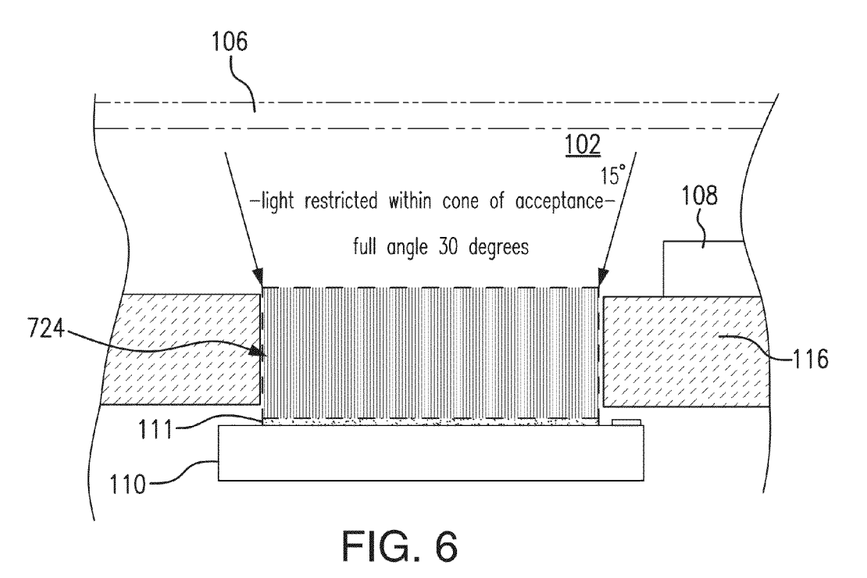
FIG. 6 is a cross-sectional view illustrating an AOI filter element, dichroic filter, and photodetector in a sensor embodying aspects of the present invention.

In some embodiments, the sensor 900 may include an angle of incidence (AOI) filter element 724, as illustrated in FIGS. 4-6, to prevent light having high angles of incidence from reaching a dichroic bandpass filter (e.g., dichroic bandpass filter 111) and may, therefore, prevent light having high angles of incidence from reaching a photodetector (e.g., signal photodetector 110).

Figure 7:
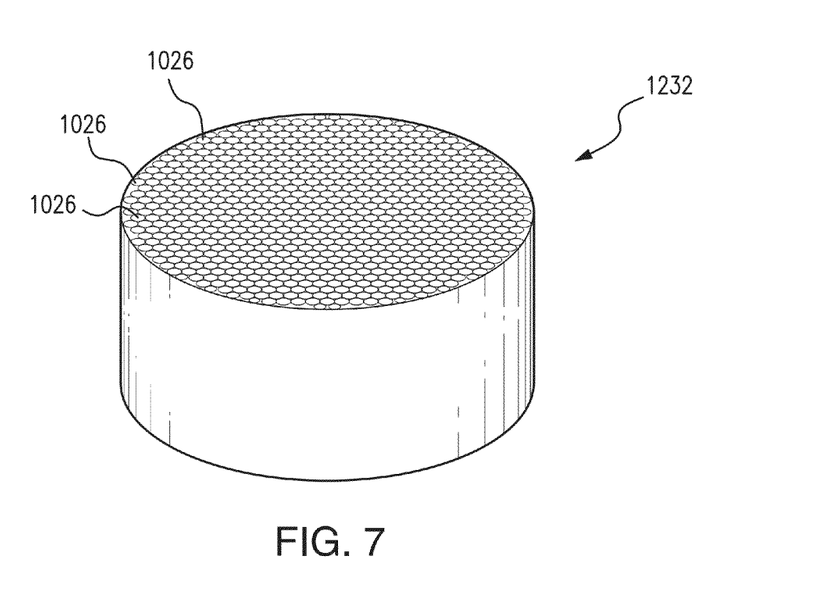
FIG. 7 illustrates a fiber optical bundle embodying aspects of the present invention.

In some embodiments, as shown in FIG. 7, the AOI filter element 724 may be a fiber optic bundle element 1232 constructed from a plurality of optical fibers 1026. The fiber optic bundle 1232 may be, for example, a coherent fiber optic bundle, which is known for use as an image conduit and for other applications. The AOI filter element 724 may be configured as an incidence angle selective precollimator (i.e., a light angle pre-filter) to restrict light access to the dichroic filter. For example, in one non-limiting embodiment, a fiber optic coherent bundle element 1232 may restrict light access to the dichroic filter to within a 30 degree cone of acceptance (i.e., a 15 degree half angle). In this example, AOIs above 15 degrees may be rejected.

In some embodiments, the AOI filter element 724 may be constructed from a coherent fiber optic bundle 1232 of the same diameter as the clad rod 220 or 222 in the existing sensor 100, and, in a non-limiting embodiment, the AOI filter element 724 may be directly substituted into the existing sensor 100 for the clad rod 220 and/or 222. However, this is not required, and, in alternative embodiments, the AOI filter element 724 may have different dimensions than the clad rod 220 or 222 in the existing sensor 100 and/or may be integrated in a sensor other than the existing sensor 100. For example, the AOI filter element 724 may be constructed to have dimensions that mate with one or more photodetectors of any size.

Figure 8:
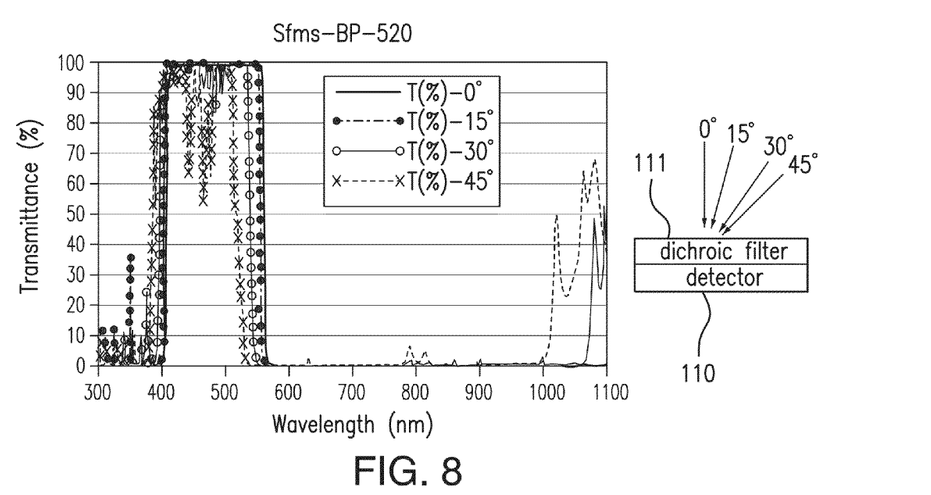
FIG. 8 is a graph illustrating the shift and degradation of a dichroic spectral profile at increasing angles of incidence in a read channel.

In some embodiments, the fiber optic bundle 1232 may be fabricated from discrete fibers 1026, which may be fused and drawn to the diameter required for the sensor. In a non-limiting embodiment, the bundle 1232 may then be sliced and polished on each end to the correct length. The fiber optical bundles 1232, after being sliced to low aspect ratios, may be fiber optic plates (FOPs). In some non-limiting embodiments, the dichroic filter (e.g., dichroic band pass filter 111 or 113) may be coated on a surface of the AOI filter element 724 (e.g., fiber optical bundle 1232, which may be a fiber optic plate). In one embodiment, as illustrated in FIGS. 7 and 8, the end of the AOI filter element 724 coated with the dichroic filter may mate to the photodetector (e.g., photodetector 110 or 112). In an alternative embodiment, the dichroic filter (e.g., dichroic band pass filter 111 or 113) may be coated on a surface of the photodetector (e.g., first photodetector 110 and/or second photodetector 112).

In some embodiments where the AOI filter element 726 is a fiber optic bundle 1232, the AOI filter element 724 may be made from different individual optical fiber sizes/diameters fused together into a coherent bundle so long as the N1 and N2 values result in the desired angle of acceptance for the dichroic filter (e.g., a 15 degree half angle).

In some embodiments, one or more fiber optic bundles 1232 (e.g., FOPs) are fabricated, polished, and cleaned and then are coated on one side with a dichroic filter (e.g., dichroic filter 111 or 113) according to the required band-pass specifications. The dichroic coated FOP may be attached to a photodetector (e.g., photodetector 110 or 112). In one embodiment, the coated side of the FOP may be joined to the photodetector surface (e.g., by gluing) and may serve to reject high angle of incidence light from entering the dichroic filter, thus allowing the dichroic filter to operate within its physical limitations imposed by the principle of thin film interference, and in turn convey only that light to the detector which is within the desired band pass spectrum required for optimum operation and performance of the optical sensor (e.g., sensor 900).

In some non-limiting embodiments, as shown in FIG. 4, the AOI filter element 724 may be incorporated in the sensor 900 having a light source 108 configured to excite indicator molecules 104 in a polymer graft 106 positioned on the surface of the sensor 900, first and second photodetectors 110 and 112 arrayed symmetrically on either side of the light source 108 to receive fluorescence for both a read channel (e.g., analyte modulation channel), and a reference channel. In alternative embodiments, the AOI filter element 724 may be applied to other sensors (e.g., sensors having other light source and photodiode configurations, sensors having a plurality of light sources, and/or sensors having a single photodetector). In one non-limiting embodiment, the sensor 900 may be identical to existing sensor 100 (described above) except that the one or more glass windows (clad rods) 220 and 222 may be replaced by one or more AOI filter elements 724.

The one or more AOI filter elements 724 may prevent or reduce unwanted light from entering the photodetectors 110 and/or 112. In particular, the one or more AOI filter elements 724 may address a physical limitation in the state of the art for dichroic thin film filter. Dichroic filters (e.g., filters 111 and 113) are thin film constructs of different refractive index materials operating on the principle of thin film interference. These filters are fabricated for very specific band pass profiles by building up successive specific layers of selected refractive index materials from within a vacuum chamber in a deposition process driven by electron beam sputtering. Such filters are very thin, on the order of 1,000 Angstroms or less and dimensionally well suited to ultraminiaturized optical sensors such as the implantable analyte (e.g., glucose) sensor. A limitation of dichroic filters is that their spectral performance is strongly affected by the angle at which light arrives at the surface of the filter. That is, dichroic filters are AOI dependent.

The successive buildup of various specific refractive index layers during the fabrication of a dichroic filter results in a strict dependence on angle of incidence to achieve the desired spectral properties. The dichroic filter achieves its best performance at a zero angle of incidence, i.e., with a ray perpendicular to the surface of the filter plane. As angles of incident light increase away from the perpendicular, the spectral selectivity is greatly diminished. FIG. 8 illustrates an example of the shift and degradation of a dichroic spectral profile at increasing AOI in the read channel, which may include dichroic filter 111 and first photodetector 110.

Figure 9:
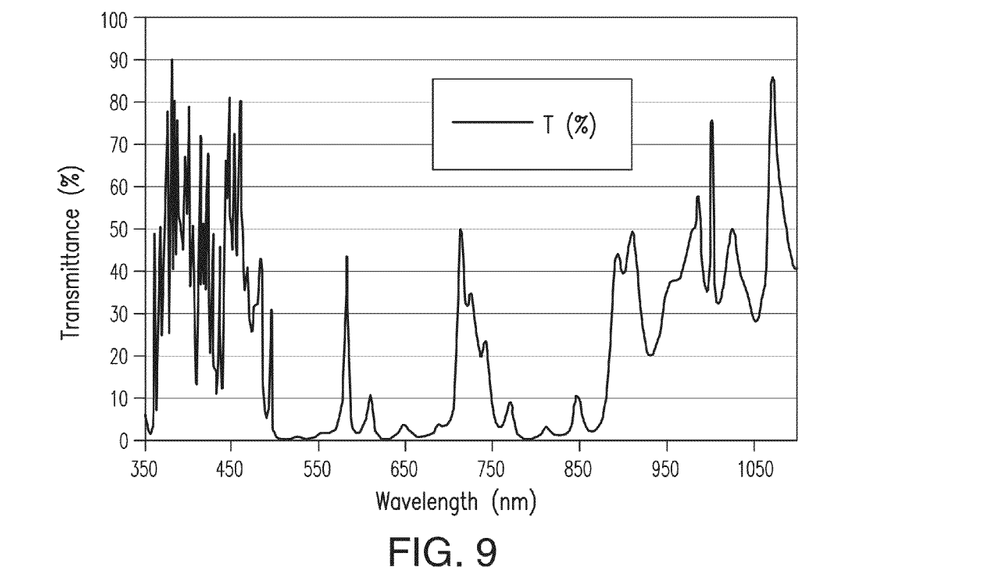
FIG. 9 is a graph illustrating transmittance versus wavelength of a dichroic filter for light entering the dichroic filter at an angle of incidence of 80 degrees.

As illustrated in the dichroic spectral profile of FIG. 8, as the AOI increases from zero through forty five degrees (and beyond), the leading and trailing edges of the band-pass region progressively shift up field toward the ultraviolet (UV), and the desired filtering profile of the dichroic filter 111 is compromised. For instance, in an embodiment in which the peak output of the light source 108 is approximately 378 nm, the peak output of the light source may be enveloped by the up-field shift. As a result, without an AOI filter element 724, unwanted excitation light 329 may be permitted to enter the pass band of the dichroic filter 111 and, therefore, enter the first/signal photodetector 110. Further, as is also shown in FIG. 8, beginning at approximately thirty degrees, and worse at forty five degrees, the downfield blocking region may begin to break down at 800 and 1,000+ nanometers. FIG. 9 illustrates an example of transmittance versus wavelength of a dichroic filter 111 for light entering the dichroic filter 111 at an angle of incidence (AOI) of 80 degrees. As shown in FIG. 9, at very high incidence values, such as eighty degrees, the dichroic filter 111 may have completely broken down and may generally allow light from almost wavelengths to enter the first photodetector 110.

Without an AOI filter element 724, light may arrive at the one or more dichroic filters 111 and 113 at very high angles of incidence (e.g., from light source backscatter, internal reflection, edge emission, and/or reflections from material surfaces). For light arriving at the one or more dichroic filters 111 and 113 at very high angles of incidence, the one or more dichroic filters 111 and 113 may not maintain any useful level of band pass selectivity. In the signal channel, the lack of a useful band pass selectivity would permit unwanted high AOI light including excitation light 129, ambient light through the skin in the 600+ nanometer range, and light from the NIR region (~700 nm to 1000 nm), along with the desired signal light from indicator fluorescence, through the filter 111 and into the first/signal photodetector 110 from high AOI, which would degrade the signal quality from the sensor 900. However, the AOI filter element 724 may prevent the unwanted high AOI light from reaching the dichroic filter 111 and, thus, prevent the unwanted high AOI light from reaching the first/signal photodetector 110.

Similarly, in embodiments of the sensor 900 having a reference channel, the performance of the sensor 900 may be degraded if light other than the intended reference light enters the second/reference channel photodetector 112. For example, in embodiments of sensor 900 that use reflected excitation light 129 as the reference light, the performance of the sensor 900 may be degraded if light other than the reflected excitation light 129 (e.g., emission light 131) enters the second/reference channel photodetector 112 and is measured thereby. For another example, in embodiments of sensor 900 that use light emitted by reference indicator molecules as the reference light, the performance of the sensor 900 may be degraded if light other than the light emitted by reference indicator molecules (e.g., reflected excitation light 129 and/or emission light 131) enters the second/reference channel photodetector 112 and is measured thereby.

In some embodiments, the sensor 900 may remain within the intended performance profile of the dichroic filter (e.g., dichroic band pass filter 111 or 113) by only allowing light within a (dichroic performance) tolerable AOI to enter the filter. As illustrated in FIG. 8, a dichroic filter design may provide optimal performance at zero degrees AOI. At fifteen degrees, there may be some shift on the leading edge, but the pass band does not yet overlap an output band of light source 108, which may, for example, be centered around approximately 378 nm. Thus, the shift at fifteen degrees can be tolerated without sacrificing overall sensor performance. However, with an AOI of 30 and 45 degrees, the up-field shift allows excitation light 129 emitted by the light source 108 (and other unwanted high AOI light) into the read channel, and the downfield blocking region begins to break down and permit longer wavelength light into the photodetector 110 outside the intended pass band. The up-field shift of the filter leading edge permits excitation light 129 to flood the photodetector 110, which can amount to a greater signal amplitude than the emission light 131 arriving from the analyte modulating indicator molecule 104. In other words, without an AOI filter element 724, the amplitude of the signal produced by signal photodetector 110 includes unwanted optical noise in addition to analyte modulating signal.

Figure 10A:
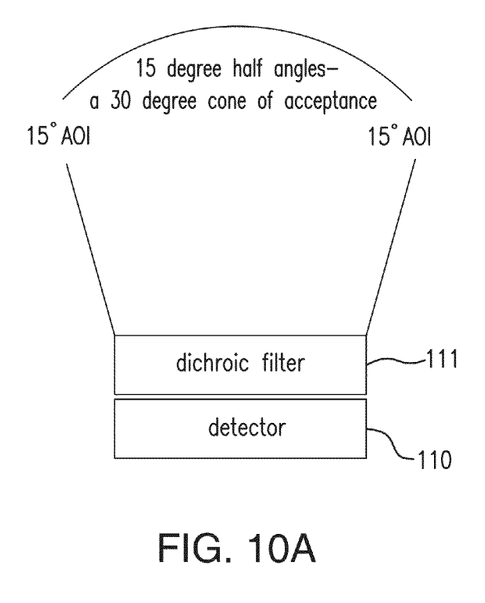
FIGS. 10A and 10B illustrate an example of a dichroic tolerable AOI and corresponding cone of acceptance for non-degraded sensor performance.
Figure 10B:
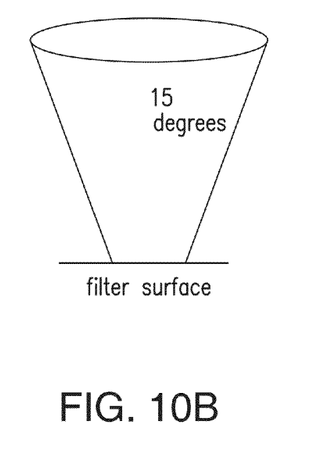

Moreover, the breakdowns in the downfield near infrared (NIR) region shown in FIG. 8 may be of particular importance for subcutaneous implantable optical sensors because this region (known as the "NIR window") is where the skin is transmissive to NIR region wavelengths and is used for medical device imaging. These NIR wavelengths may penetrate as deep as 10 cm into human tissue. Without adequate filtering, sunlight can penetrate the skin at these wavelengths and cause highly variable interference for the sensor's photodiode detectors (e.g., photodetectors 110 and/or 112), which unfiltered, are sensitive up through a peak of about 1100 nanometers. These unwanted light sources can overwhelm a signal processing system because they are uncontrolled and variable in a way that cannot be predicted and compensated for by signal processing. Removing these unwanted optical interferences serves to increase SNR with direct positive impact on device accuracy, longevity, sensitivity, and mean absolute relative difference (MARD). If light entering the dichroic filter can be restricted to within an angular profile within an appropriate AOI threshold (e.g., within approximately 15 degrees angle of incidence), the dichroic filter can then function effectively within its physical limitations to eliminate unwanted interference light. As illustrated in FIGS. 10A and 10B, for a field of view restricted to a numerical aperture of 15 degree incident angle acceptance, the overall field of view is a 30 degree cone of acceptance.

As illustrated in FIGS. 4-6, in some embodiments, the sensor 900 may include an angle of incidence filter element 724 (i.e., an optical AOI pre-filter) to reject angles of incidence above a threshold value (e.g., ~15 degrees) AOI and permit through only those angles lower than the threshold value AOI such that the dichroic band pass filter (e.g., dichroic filter 111 or 113) can then pass only those wavelengths within the intended optical band-pass profile by design on to the photodetector (e.g., photodetector 110 or 112).

In some embodiments, the angle of incidence filter element 724 (i.e., optical AOI pre-filter) may be constructed to accept only light within a cone of acceptance of ~30 degrees and reject light arriving at the surface from outside the ~30 degree acceptance cone. The accepted light may then be permitted into the dichroic filter (e.g., dichroic filter 111 or 113), which then further filters the low AOI light to its intended pass band, which is in turn passed to the photodetector (e.g., photodetector 110 or 112).

Figure 11:
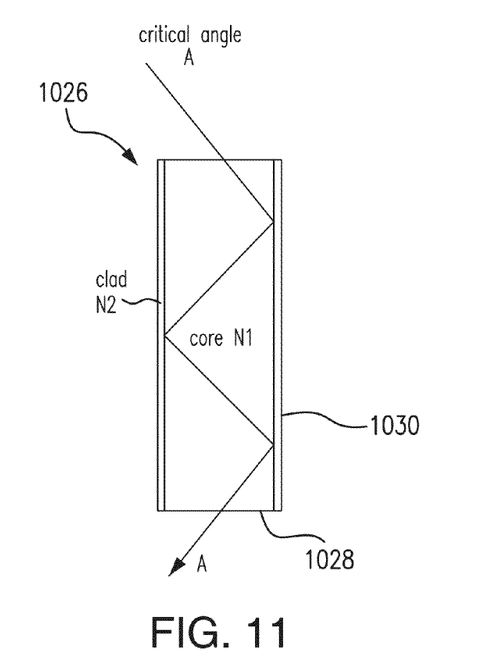
FIG. 11 illustrates an optical fiber having a core with a core refractive index $N_1$, a cladding with a cladding refractive index $N_2$, and a critical angle A.
Figure 12:
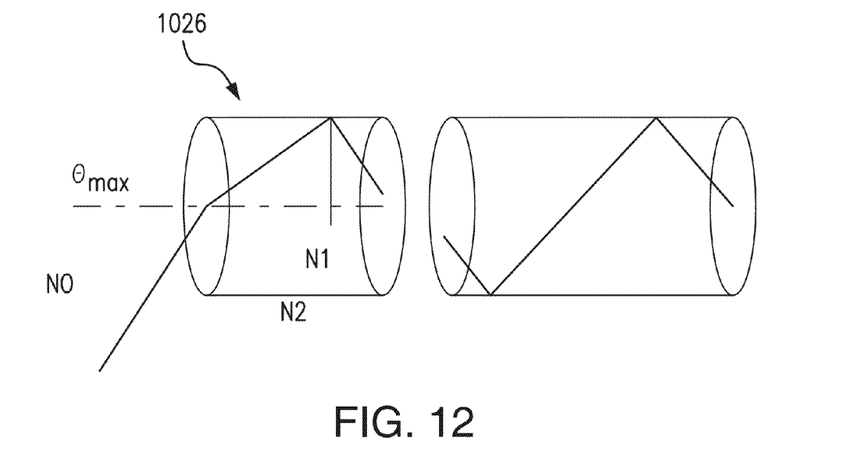
FIG. 12 illustrates an optical fiber having a core refractive index $N_1$ and a clad refractive index $N_2$ that is surrounded by a substance having a refractive index $N_0$.

In some embodiments, as illustrated in FIG. 7, the angle of incidence filter element 724 may be an optical fiber bundle 1232 including one or more optical fibers 1026. An optical fiber 1026 operates on the principle of total internal reflection. As shown in FIGS. 11 and 12, the optical fiber 724 may include a core 1028 having a high refractive index, the AOI filter element 724 may restrict angles of acceptance using Snell's Law and the Principle of Total Internal Reflectance. The core 1028 may be surrounded by a cladding 1030 having of lower refractive index such that, under Snell's Law, incident light below the critical angle as defined by the refractive indices (core and clad) is propagated through the medium.

The critical angle, as defined by the refractive index values of the core 1028 and clad 1030, is the maximum angle of light which can be carried by the fiber 1026. Angles exceeding the critical angle will not be propagated by the fiber 1026. The relative values of these refractive indices establish the numerical aperture of the fiber 1026. The numerical aperture for any fiber 1026 is determined from the refractive index of the core ($N_1$) and of the clad ($N_2$). Thus, by specifying core and cladding refractive index values, specific acceptance angles may be achieved. FIG. 11 illustrates an optical fiber 1026 having a core 1028 with a core refractive index $N_1$, a cladding 1030 with a cladding refractive index $N_2$, and a critical angle A. The acceptance angle of the optical fiber 1026 may be calculated by (i) determining the numerical aperture NA of the optical fiber using the core's refractive index $N_1$ and the cladding's refractive index $N_2$ according to the formula NA=$\sqrt{N_1^2-N_2^2}$; (ii) finding the critical angle A (in degrees), which is equal to the arc sin (sin−1) of the numerical aperture NA; and (iii) multiplying the critical angle by two (i.e., the acceptance angle=2A). The critical angle A is the same for rays entering or exiting the fiber 1026.

An optical fiber 1026, which is a specific combination of refractive index values $N_1$ and $N_2$ for the core 1028 and clad 1030, respectively, will only accept light arriving within the maximum value of the critical angle A. Any values of $N_1$ and $N_2$ that result in a desired critical angle. In some embodiments, the critical angle may be approximately 15 degrees and/or generally less than 20 degrees.

In some embodiments, the refractive index surrounding the fiber 1028 may be air, but this is not required. For example, in other embodiments, an optical potting epoxy may surround the part within the sensor housing 102. This refractive index value may also effect the determination and design of the critical angle. FIG. 12 illustrates an optical fiber 1026 having a core refractive index $N_1$ and a clad refractive index $N_2$ that is surrounded by a substance (e.g., air or potting epoxy) having a refractive index $N_0$ (i.e., the ambient refractive index). The acceptance half angle $\theta_{max}$ of the optical fiber 1026 may be calculated using formula $\sin \theta_{max} = \sqrt{((N_1^2 - N_2^2)/N_0)}$.

In some embodiments where the AOI filter element 726 is a fiber optic bundle 1232 constructed from a plurality of optical fibers 1026, the optical fibers 1026 of the bundle 1232 may be of any diameter and may, for example, be fused together by heat to make one large optical conduit. Each fiber 1026 within a bundle 1232 may convey light from one end to the other. If each optical fiber 1026 within the bundle 1232 is produced with a core and clad refractive index such that the acceptance angle for each fiber 1026 is limited to a threshold angle of incidence (e.g., 15 degrees half angle or, in other words, a 30 degree cone of acceptance), then a bundle 1232 made from these fibers 1026 will also have an acceptance angle limited to the threshold angle.

Some existing sensors (e.g., existing sensor 100) may use a clad rod (e.g., clad rod 220 or 222 of FIG. 2) to capture and convey light to the detectors. A clad rod may be thought of as a very big fiber or simply a glass rod with a cladding. However, the dimensions and aspect ratio of the clad rod 220 or 222 and the refractive index values N1 and N2 of the core and cladding result in a cone of acceptance of no less than approximately 55 degrees.

At permissible AOI values of as much as 55 degrees, the dichroic filter 111 coated on the surface of the photodetector 110 is severely compromised and cannot provide the band pass filter cut required for best performance. This deficiency may appear subtle in performance data for the existing sensor 100 because the existing sensor 100 has an intrinsically good signal to noise ratio (SNR) and shows good correlation with clinical data implanted in humans. However, the subtle manifestation of the deficiency may be apparent in signal processing. In the existing sensor 100, it is difficult to adequately predict and correct for unwanted light permitted into the photodetectors 110 and 112 (e.g., unwanted excitation light 129 from the light source 108 and/or ambient light passing through the skin permitted into signal photodetector 110). Pre-collimation, by an AOI filter element 724, of light incident on a photodetector prior to the dichroic filtering may address this unwanted and variable signal amplitude (e.g., due to variable backscatter and ambient light values in the signal channel) by creating a means whereby the dichroic filter can operate within its physical limitations and according to the actual design intended pass band specification for each channel.

The dichroic filters 111 and 113 are effective at preventing low AOI light having a wavelength outside the intended pass band from reaching the photodectors 110 and 112, respectively. However, physical limitations of the dichroic filters 111 and 113 may preclude the dichroic filters 111 and 113 from preventing high AOI light having a wavelength outside the intended pass band from reaching the photodetectors 110 and 112, respectively. The AOI filter element 724 may reduce or prevent degradation of the performance of the sensor 900 caused by unwanted high AOI light that reaches a photodetector 110 or 112 by preventing the unwanted high AOI light from reaching the dichroic band pass filter 110 or 112 and, thereby, preventing the unwanted high AOI light from reaching the photodetectors 110 and 112.

As illustrated in FIGS. 5 and 6, in some non-limiting embodiments, the AOI filter element 726 may only accept light from within an approximately 30 degree cone of acceptance (i.e., a 15 degree half-angle or angle of incidence) and may convey that light to the dichroic filter 111, which may be coated on the opposite end of the AOI filter element 726 (e.g., fiber optic bundle 1232) nearest the photodetector 110 such that the dichroic filter 111 will only receive light within a 15 degree AOI (e.g., through the individual optical fiber elements 1026 of the bundle 1232). The dichroic filter 111 may then filter the low angle incident light by operating within its physical limitations according to the band pass specifications established by designers as optimal for sensor performance.

In some embodiments, there may be some tradeoff between analyte modulated signal amplitude and unwanted interference signal amplitude by using of the combination of the AOI filter element 724 (i.e., the pre-collimator) and the dichroic filter 111 because the AOI filter element 724 cannot discriminate between high angle analyte (e.g., glucose) modulated emission light 131 and high angle non-modulated interference light (e.g., excitation light 131 and/or ambient light). That is, in some embodiments, the AOI filter element 724 may only discriminate on angle of incidence (e.g., to within the optimal acceptance angles of the dichroic filter 111). Desirable analyte modulated emission light 131 light arriving from bounced or scattered incidence angles exceeding the threshold angle (e.g., 15 degrees) may also be rejected along with the unwanted high angle intereference light. The net gain however in signal to noise may provide considerable benefit by eliminating a variable noise source.

In some embodiments, AOI filter element 724 may be configured to prevent light having an angle of incidence greater than a threshold angle from reaching the dichroic band pass 111 or 113 filter and to propagate light having an angle of incidence less than the threshold angle to the dichroic band pass filter 111 or 113. In some non-limiting embodiments, including the embodiment illustrated in FIGS. 7 and 8, the threshold angle is 15 degrees, which produces a cone of acceptance of 30 degrees. However, this is not required, and, in alternative embodiments, other threshold angles and, therefore, other cones of acceptance may be used. For instance, in some non-limiting embodiments, the threshold angle may be less than or equal 20 degrees and greater than or equal to 5 degrees. In some non-limiting embodiments, the threshold angle may be less than or equal to 20 degrees and greater than or equal to 10 degrees. In some non-limiting embodiments, the threshold angle may be less than or equal to 17 degrees and greater than or equal to 12 degrees. In one non-limiting embodiments, the threshold angle may be 10 degrees. In another non-limiting embodiment, the threshold angle may be 18 degrees.

Moreover, in some embodiments, in practice, there may be a tolerance (e.g., ±2 or 3 degrees) in the threshold angle dividing the angles of incidence propagated by the AOI filter element 724 to the dichroic filter 111 or 113 and the angles of incidence prevented by the AOI filter element 724 from reaching the dichroic filter 111 or 113. For instance, in a non-limiting embodiment having an AOI filter element 724 with a threshold angle of 15 degrees and a tolerance of ±3 degrees, the AOI filter element 724 may prevent a small amount of light having an AOI of 12 degrees from reaching the dichroic filter 111 or 113 and may fully prevent light having an AOI of 18 degrees or more from reaching the dichroic filter 111 or 113.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, in the embodiments described above, the AOI filter element 724 and dichroic filter 111 or 113 are incorporated in a sensor. However, this is not required, and, in some alternative embodiments, the AOI filter element 724 and dichroic filter 111 or 113 may be incorporated into other apparatuses, such as, for example, imaging systems and/or lighting devices.

What is claimed is:

1. A sensor comprising:
   a sensor housing;
   a graft on at least a portion of an exterior surface of the sensor housing;
   indicator molecules distributed throughout the graft and configured to emit emission light at least to the receiving surface of the angle of incidence filter element;
   a light source contained within the sensor housing and configured to irradiate excitation light to the indicator molecules;
   a photodetector contained within the sensor housing and configured to convert received light into current indicative of the intensity of the received light;
   a dichroic band pass filter contained within the sensor housing and configured to prevent light having a wavelength outside a band pass region from reaching the photodetector and to pass light having a wavelength within the band pass region to the photodetector; and
   an angle of incidence filter element contained within the sensor housing, comprising a receiving surface, and configured to prevent light having an angle of incidence relative to an axis perpendicular to the receiving surface greater than a threshold angle from reaching the dichroic band pass filter and to propagate light having an angle of incidence relative to the axis perpendicular to the receiving surface less than the threshold angle to the dichroic band pass filter;
   wherein the angle of incidence filter element is a fiber optic bundle comprising a plurality of optical fibers.

2. The sensor of claim 1, wherein each of the plurality of optical fibers comprises:
   a core having a first refractive index; and
   a clad having a second refractive index that is lower than the first refractive index;
   wherein a relative value of the first and second refractive indices defines the threshold angle.

3. The sensor of claim 1, wherein the fiber optical bundle has been cut into a fiber optic plate.

4. The sensor of claim 1, wherein the indicator molecules are positioned relative to the receiving surface of the angle of incidence filter element such that at least a portion of the emission light reaches the receiving surface of the angle of incidence filter element with an angle of incidence relative to the axis perpendicular to the receiving surface less than the threshold angle.

5. The sensor of claim 1, wherein the dichroic band pass filter is a thin film dichroic band pass filter.

6. The sensor of claim 1, wherein the dichroic band pass filter is coated on the angle of incidence filter element.

7. The sensor of claim 6, wherein the angle of incidence filter element comprises an exit surface opposite the receiving surface, and the dichroic band pass filter is coated on the exit surface of the angle of incidence filter element.

8. The sensor of claim 1, wherein the dichroic band pass filter is coated on the photodetector.

9. The sensor of claim 1, wherein the photodetector is a photodiode.

10. The sensor of claim 1, wherein the threshold angle is less than or equal 25 degrees and greater than or equal to 5 degrees.

11. The sensor of claim 10, wherein the threshold angle is less than or equal to 20 degrees and greater than or equal to 10 degrees.

12. The sensor of claim 11, wherein the threshold angle is less than or equal to 17 degrees and greater than or equal to 12 degrees.

13. The sensor of claim 12, wherein the threshold angle is 15 degrees.

14. The sensor of claim 10, wherein the threshold angle is 10 degrees.

15. The sensor of claim 1, wherein the threshold angle is less than or equal to an angle of incidence relative to the axis perpendicular to the receiving surface of the angle of incidence filter element at which the spectral performance of the dichroic band pass filter begins to break down.

16. The sensor of claim 1, wherein the threshold angle is configured to optimize the optical signal to noise ratio (SNR) of the light received by the photodetector, analyte modulated light is the signal, and all other unwanted incident light is the noise.

17. The sensor of claim 1, wherein the photodetector is a first photodetector, the dichroic band pass filter is a first dichroic band pass filter, the band pass region is a first band-pass region, the receiving surface is a first receiving surface, the threshold angle is a first threshold angle, and the sensor comprises:
   a second photodetector configured to convert received light into current indicative of the intensity of the light received by the second photodetector;
   a second dichroic band pass filter configured to prevent light having a wavelength outside a second band pass region from reaching the second photodetector and to pass light having a wavelength within the second band pass region to the second photodetector; and
   a second angle of incidence filter element comprising a second receiving surface and configured to prevent light having an angle of incidence relative to an axis perpendicular to the second receiving surface greater than a second threshold angle from reaching the second dichroic band pass filter and to propagate light having an angle of incidence relative to the axis perpendicular to the second receiving surface less than the second threshold angle to the second dichroic band pass filter.

18. The sensor of claim 1, wherein the sensor is a glucose sensor.

19. The sensor of claim 1, wherein the sensor is an oxygen sensor.

20. The sensor of claim 1, wherein the sensor is an implantable sensor configured for implantation into a living animal.

21. The sensor of claim 20, wherein the implantable sensor is configured for implantation into a living human.

22. A method of detecting the concentration of an analyte using a sensor comprising a sensor housing, a graft on at least a portion of an exterior surface of the sensor housing, a light source contained within the sensor housing, indicator molecules distributed throughout the graft, an angle of incidence filter element contained within the sensor housing, a dichroic band pass filter contained within the sensor housing, and a photodetector contained within the sensor housing; the method comprising:
- irradiating, by the light source, excitation light to the indicator molecules;
- emitting, by the indicator molecules, emission light to the angle of incidence filter element;
- receiving, by a receiving surface of the angle of incidence filter element, light including the emission light;
- preventing, by the angle of incidence filter element, light of the received light having an angle of incidence greater than a threshold angle relative to an axis perpendicular to the receiving surface from reaching the dichroic band pass filter;
- propagating, by the angle of incidence filter element, light of the received light having an angle of incidence less than the threshold angle relative to the axis perpendicular to the receiving surface;
- preventing, by the dichroic band pass filter, light of the propagated light having a wavelength outside a band pass region of the dichroic band pass filter from reaching the photodetector;
- passing, by the dichroic band pass filter, light of the propagated light having a wavelength within the band pass region of the dichroic band pass filter to the photodetector; and
- receiving, by the photodetector, the passed light;
- wherein the angle of incidence filter element is a fiber optic bundle comprising a plurality of optical fibers.

23. The method of claim 22, wherein each of the plurality of optical fibers comprises a core and a clad having refractive indices whose relative value defines the threshold angle.

24. The method of claim 22, wherein the fiber optical bundle has been cut into a fiber optic plate.

25. The method of claim 22, wherein at least a portion of the emission light reaches the receiving surface of the angle of incidence filter element with an angle of incidence relative to the axis perpendicular to the receiving surface less than the threshold angle.

26. The method of claim 22, wherein the threshold angle is less than or equal 20 degrees and greater than or equal to 5 degrees.

27. The method of claim 26, wherein the threshold angle is less than or equal to 20 degrees and greater than or equal to 10 degrees.

28. The method of claim 26, wherein the threshold angle is less than or equal to 17 degrees and greater than or equal to 12 degrees.

29. The method of claim 28, wherein the threshold angle is 15 degrees.

30. The method of claim 26, wherein the threshold angle is 10 degrees.

31. The method of claim 26, wherein the threshold angle is 20 degrees.

32. The method of claim 22, wherein the threshold angle is less than or equal to an angle of incidence relative to the axis perpendicular to the receiving surface of the angle of incidence filter element at which the spectral performance of the dichroic band pass filter begins to break down.

33. The method of claim 22, wherein the threshold angle is configured to optimize the optical signal to noise ratio (SNR) of the light received by the photodetector, analyte modulated light is the signal, and all other unwanted incident light is the noise.

* * * * *